(12) United States Patent
Feng et al.

(10) Patent No.: US 11,487,029 B2
(45) Date of Patent: Nov. 1, 2022

(54) SYSTEMS AND METHODS FOR POSITRON EMISSION TOMOGRAPHY IMAGE RECONSTRUCTION

(71) Applicant: SHANGHAI UNITED IMAGING HEALTHCARE CO., LTD., Shanghai (CN)

(72) Inventors: Tao Feng, Houston, TX (US); Gang Yang, Shanghai (CN); Hao Liu, Shanghai (CN); Yang Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 42 days.

(21) Appl. No.: 17/003,950

(22) Filed: Aug. 26, 2020

(65) Prior Publication Data
US 2020/0393579 A1 Dec. 17, 2020

(51) Int. Cl.
*G01T 1/29* (2006.01)
*G06T 11/00* (2006.01)
*A61B 6/03* (2006.01)

(52) U.S. Cl.
CPC .......... *G01T 1/2985* (2013.01); *G06T 11/003* (2013.01); *A61B 6/037* (2013.01); *G06T 2207/10104* (2013.01)

(58) Field of Classification Search
CPC ................ G01T 1/2985; G06T 11/003; G06T 2207/10104; G06T 11/005; G06T 2211/412; A61B 6/037; A61B 6/461; A61B 6/527; A61B 6/5211; A61B 6/5264; A61B 6/03; A61B 6/5288; A61B 6/566
See application file for complete search history.

(56) References Cited

U.S. PATENT DOCUMENTS

2016/0078619 A1 * 3/2016 Hsieh ...................... A61B 6/545
378/4
2018/0174360 A1 * 6/2018 Feng ..................... A61B 6/5264

FOREIGN PATENT DOCUMENTS

WO WO-2018172229 A1 * 9/2018 ............... A61B 5/08

* cited by examiner

*Primary Examiner* — David P Porta
*Assistant Examiner* — Mamadou Faye
(74) *Attorney, Agent, or Firm* — Metis IP LLC

(57) ABSTRACT

The present disclosure is related to systems and methods for reconstructing a positron emission tomography (PET) image. The method includes obtaining PET data of a subject. The PET data may correspond to a plurality of voxels in a reconstructed image domain. The method includes obtaining a motion signal of the subject. The method includes obtaining motion amplitude data. The motion amplitude data may indicate a motion range for each voxel of the plurality of voxels. The method includes determining gating data based at least in part on the motion amplitude data. The gating data may include useful percentage counts each of which corresponds to at least one voxel of the plurality of voxels. The method includes gating the PET data based on the gating data and the motion signal. The method includes reconstructing a PET image of the subject based on the gated PET data.

20 Claims, 7 Drawing Sheets

SYSTEMS AND METHODS FOR POSITRON EMISSION TOMOGRAPHY IMAGE RECONSTRUCTION

TECHNICAL FIELD

This disclosure generally relates to systems and methods for image reconstruction, and more particularly, relates to systems and methods for reconstructing a positron emission tomography (PET) image.

BACKGROUND

Motions (e.g., a respiratory motion, a cardiac motion) during PET scans can cause resolution degradation and introduce artifacts in a PET image that affect diagnoses performed on the basis of the PET image. For example, the respiratory motion of a subject leads to motion artifacts and blurring in the PET image, which hinders an accurate detection, localization and quantification of possible lesions and tumors. Respiratory gating techniques have been developed to reduce motion blurring effects by dividing PET data into a plurality of bins or sections based on a motion signal. Each section corresponds to a certain respiratory phase with reduced motion blurring. Since each section only contains a fraction of the total count of detected coincidence events, the gain in resolving involuntary motion through gating is compromised by the increase of noise when the PET data is divided into too many bins. Thus, it is desirable to develop methods and systems for reconstructing data acquired by a scanner with reduced motion blur without over-gating of a region of the subject that is not significantly affected by a motion of the subject during the scanning.

SUMMARY

According to an aspect of the present disclosure, a method for reconstructing a positron emission tomography (PET) image may be implemented on a computing device having one or more processors and one or more storage devices. The method may include obtaining PET data of a subject. The PET data may correspond to a plurality of voxels in a reconstructed image domain. The method may include obtaining a motion signal of the subject. The method may include obtaining motion amplitude data. The motion amplitude data may indicate a motion range for each voxel of the plurality of voxels. The method may include determining gating data based at least in part on the motion amplitude data. The gating data may include useful percentage counts each of which corresponds to at least one voxel of the plurality of voxels. The method may include gating the PET data based on the gating data and the motion signal. The method may include reconstructing a PET image of the subject based on the gated PET data.

In some embodiments, the method may include obtaining an attenuation map of the subject. The method may include determining the motion amplitude data based on the attenuation map.

In some embodiments, the method may include determining a plurality of intermediate images based on the PET data. The method may include determining a vector field for the plurality of voxels based on the plurality of intermediate images. The method may include determining the motion amplitude data based on the vector field.

In some embodiments, the plurality of intermediate images may be determined by performing a back-projection operation on the PET data.

In some embodiments, the plurality of intermediate images may be reconstructed by gating the PET data.

In some embodiments, the method may include obtaining a motion amplitude threshold. The method may include determining the gating data based on the motion amplitude data and the motion amplitude threshold.

In some embodiments, the motion amplitude threshold may relate to a desired spatial resolution of the reconstructed PET image.

In some embodiments, the method may include determining first processed motion amplitude data by performing a maximum intensity projection operation on the motion amplitude data. The method may include determining the gating data based on the first processed motion amplitude data and the motion amplitude threshold.

In some embodiments, the method may include determining second processed motion amplitude data by performing a projection operation on the motion amplitude data. The method may include determining the gating data based on the second processed motion amplitude data and the motion amplitude threshold.

In some embodiments, the method may include, for each voxel of the plurality of voxels, determining a useful percentage count for the voxel based on a motion range for the voxel and the motion amplitude threshold.

In some embodiments, the PET data may include TOF information. The PET data may correspond to a plurality of lines of response (LORs). Each LOR of the plurality of LORs may include a plurality of bins. Each bin of the plurality of bins may correspond to at least one voxel of the plurality of voxels in the reconstructed image domain. A length of each bin may relate to the TOF information. The method may include, for each LOR of the plurality of LORs, determining a useful percentage count for the each bin of the plurality of bins based on the motion amplitude data, the motion amplitude threshold, and the TOF information.

In some embodiments, a first motion range for a first voxel may correspond to a first useful percentage count. A second motion range for a second voxel may correspond to a second useful percentage count. The first useful percentage count may be different from the second useful percentage count.

In some embodiments, the first motion range may be greater than the second motion range. The first useful percentage count may be lower than the second useful percentage count.

According to an aspect of the present disclosure, a system for reconstructing a positron emission tomography (PET) image may include at least one storage device storing a set of instructions, and at least one processor in communication with the at least one storage device. When executing the stored set of instructions, the at least one processor may cause the system to perform a method. The method may include obtaining PET data of a subject. The PET data may correspond to a plurality of voxels in a reconstructed image domain. The method may include obtaining a motion signal of the subject. The method may include obtaining motion amplitude data. The motion amplitude data may indicate a motion range for each voxel of the plurality of voxels. The method may include determining gating data based at least in part on the motion amplitude data. The gating data may include useful percentage counts each of which corresponds to at least one voxel of the plurality of voxels. The method may include gating the PET data based on the gating data and the motion signal. The method may include reconstructing a PET image of the subject based on the gated PET data.

In some embodiments, the method may include obtaining an attenuation map of the subject. The method may include determining the motion amplitude data based on the attenuation map.

In some embodiments, the method may include determining a plurality of intermediate images based on the PET data. The method may include determining a vector field for the plurality of voxels based on the plurality of intermediate images. The method may include determining the motion amplitude data based on the vector field.

In some embodiments, the plurality of intermediate images may be determined by performing a back-projection operation on the PET data.

In some embodiments, the plurality of intermediate images may be reconstructed by gating the PET data.

In some embodiments, the method may include obtaining a motion amplitude threshold. The method may include determining the gating data based on the motion amplitude data and the motion amplitude threshold.

According to still another aspect of the present disclosure, a non-transitory computer readable medium may include at least one set of instructions. When executed by at least one processor of a computing device, the at least one set of instructions may cause the at least one processor to effectuate a method. The method may include obtaining PET data of a subject. The PET data may correspond to a plurality of voxels in a reconstructed image domain. The method may include obtaining a motion signal of the subject. The method may include obtaining motion amplitude data. The motion amplitude data may indicate a motion range for each voxel of the plurality of voxels. The method may include determining gating data based at least in part on the motion amplitude data. The gating data may include useful percentage counts each of which corresponds to at least one voxel of the plurality of voxels. The method may include gating the PET data based on the gating data and the motion signal. The method may include reconstructing a PET image of the subject based on the gated PET data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
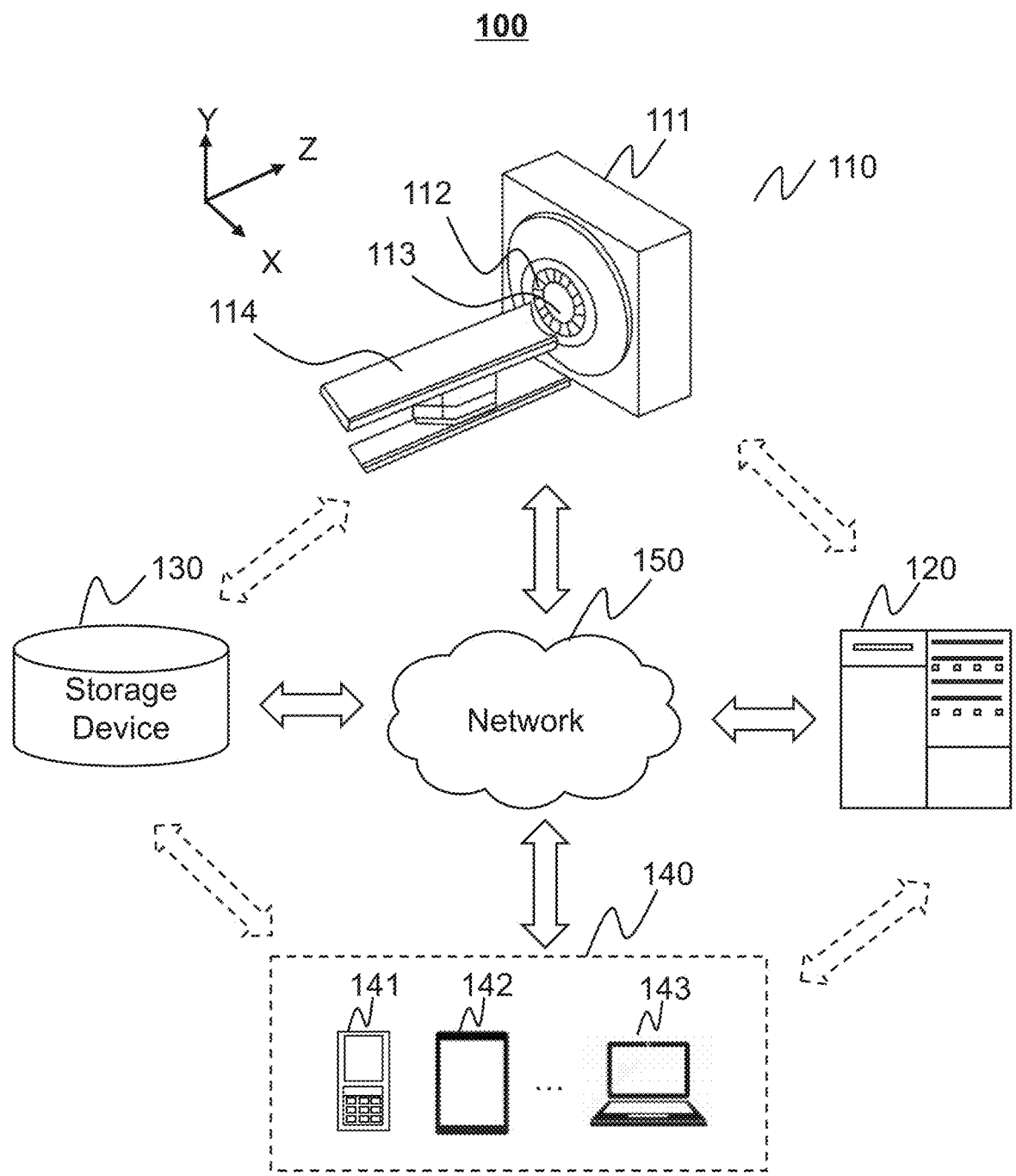
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "anatomical structure" in the present disclosure may refer to gas (e.g., air), liquid (e.g., water), solid (e.g., stone), cell, tissue, organ of a subject, or any combination thereof, which may be displayed in an image and really exist in or on the subject's body. The term "region," "location," and "area" in the present disclosure may refer to a location of an anatomical structure shown in the image or an actual location of the anatomical structure existing in or on the subject's body, since the image may indicate the actual location of a certain anatomical structure existing in or on the subject's body.

Provided herein are systems and components for imaging, such as for disease diagnosis, treatment, or research purposes. In some embodiments, the imaging system may be a positron emission tomography (PET) system, a single photon emission computed tomography (SPECT) system, a computed tomography-positron emission tomography (CT-PET) system, a magnetic resonance-positron emission tomography (MR-PET) system, or the like. For illustration purposes, the disclosure describes systems and methods for PET image reconstruction. It is understood that this is for illustration purposes and not intended to limit the scope of the present disclosure. The imaging system may reconstruct a PET image based on a gating approach. As used herein, a gating approach refers to that PET data are divided into a plurality of sections or bins at least one of which may be selected to be processed to generate a PET image.

In a traditional gating technique, a pre-determined number or count of gates may be used for a whole field of view (FOV). Various regions of the entire body of the subject may move to various degrees during the scanning of the subject. For example, noticeable motions may occur only in selected regions of the body such as the chest and the abdomen. A fixed gate number or count is hardly suitable for every region. As a result, a region with a small or negligible motion may be subject to unnecessary over-gating, while a region with a large motion may suffer from noticeable blurring. This effect is especially severe for a system with a large FOV, such as a whole-body PET scanner.

An aspect of the present disclosure relates to a system and method for PET image reconstruction. According to some embodiments of the present disclosure, a processing device may obtain PET data of a subject. The PET data may correspond to a plurality of voxels in a reconstructed image domain. The processing device may obtain a motion signal of the subject. The processing device may obtain motion amplitude data. The motion amplitude data may indicate a motion range for each voxel of the plurality of voxels. The processing device may determine gating data based at least in part on the motion amplitude data. The gating data may include useful percentage counts each of which corresponds to at least one voxel of the plurality of voxels. The processing device may gate the PET data based on the gating data and the motion signal. The processing device may reconstruct a PET image of the subject based on the gated PET data.

Accordingly, considering that the motion ranges of different spatial points of the subject may be different, different gate numbers or different useful percentage counts for PET data acquired from different spatial points of the subject that correspond to different voxels in the reconstructed image domain may be determined. That is, the gate number or useful percentage of counts of a region may be locally adaptive to local motion amplitude, thereby achieving a locally adaptive gating in PET. The quality of the PET image reconstructed based on the locally adaptive gating data may be improved.

FIG. 1 is a schematic diagram illustrating an exemplary imaging system according to some embodiments of the present disclosure. As illustrated, the imaging system 100 may include an imaging device 110, a processing device 120, a storage device 130, a terminal 140, and a network 150. The components of the imaging system 100 may be connected in one or more of various ways. Merely by way of example, as illustrated in FIG. 1, the imaging device 110 may be connected to the processing device 120 directly as indicated by the bi-directional arrow in dotted lines linking the imaging device 110 and the processing device 120, or through the network 150. As another example, the storage device 130 may be connected to the imaging device 110 directly as indicated by the bi-directional arrow in dotted lines linking the imaging device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

In some embodiments, the imaging device 110 may scan a subject, and acquire data relating to the subject. In some embodiments, the imaging device 110 may be an emission computed tomography (ECT) device, a positron emission tomography (PET) device, a single photon emission computed tomography (SPECT) device, a multi-modality device, or the like, or any combination thereof. Exemplary multi-modality device may include a CT-PET device, an MR-PET device, or the like. In some embodiments, the multi-modality imaging device may include modules and/or components for performing PET imaging and/or related analysis.

In some embodiments, the imaging device 110 may be a PET device including a gantry 111, a detector 112, a detection region 113, and a table 114. In the present disclosure, as shown in FIG. 1, a positive X axis direction may be from the left side to the right side of the gantry 111 viewed from the direction facing the front of the imaging device 110. A positive Y axis direction may be from the lower part (or from the floor where the imaging device 110 stands) to the upper part of the gantry 111. A positive Z axis direction may be the direction in which the table is moved from the outside into the imaging device 110 viewed from the direction facing the front of the imaging device 110. The gantry 111 may support the detector 112. A subject may be placed on the table 114 and moved into the detection region 113 for scanning along the Z axis as illustrated in FIG. 1. The detector 112 may detect radiation events (e.g., gamma photons) emitted from the detection region 113. In some embodiments, the detector 112 may include one or more detector units. The detector 112 may include a scintillation detector (e.g., a cesium iodide detector), a gas detector, etc. The detector 112 may be and/or include a single-row detector in which a plurality of detector units are arranged in a single row and/or a multi-row detector in which a plurality of detector units are arranged in multiple rows.

In some embodiments, the imaging device 110 may be a single-bed whole-body PET device. Using a single-bed whole-body PET device, a subject may be scanned at one bed position to obtain projection data relating to a whole (total) body of a subject in a whole field of view (FOV) without the need to move the bed on which the subject is supported during the scan. The whole FOV may cover the whole body of the subject. In some embodiments, the whole FOV may include a plurality of local volumes of interest (VOIs). A local VOI may cover a part or region of the subject.

The processing device 120 may process data and/or information obtained from the imaging device 110, the storage device 130, and/or the terminal(s) 140. For example, the processing device 120 may obtain PET data of a subject. As another example, the processing device 120 may obtain a motion signal of a subject. As another example, the processing device 120 may obtain motion amplitude data. The motion amplitude data may indicate a motion range for each voxel of a plurality of voxels in a reconstructed image domain. As still another example, the processing device 120 may determine gating data based at least in part on motion amplitude data. The gating data may include useful percentage counts each of which corresponds to at least one voxel of a plurality of voxels in a reconstructed image domain. As still another example, the processing device 120 may gate PET data based on gating data and a motion signal. As still another example, the processing device 120 may reconstruct a PET image of a subject based on gated PET data.

In some embodiments, the processing device 120 may be a single server or a server group. The server group may be centralized or distributed. In some embodiments, the processing device 120 may be local or remote. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the imaging device 110.

The storage device 130 may store data, instructions, and/or any other information. In some embodiments, the storage device 130 may store data obtained from the imaging device 110, the processing device 120, and/or the terminal(s) 140. The data may include image data acquired by the processing device 120, algorithms and/or models for processing the image data, etc. For example, the storage device 130 may store PET data of a subject obtained from a PET device (e.g., the imaging device 110). As another example, the storage device 130 may store a motion signal determined by the processing device 120. As still another example, the storage device 130 may store motion amplitude data determined by the processing device 120. As still another example, the storage device 130 may store gating data determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the imaging system 100 (e.g., the processing device 120, the terminal(s) 140). One or more components in the imaging system 100 may access the data or instructions stored in the storage device 130 via the network 150. In some embodiments, the storage device 130 may be integrated into the imaging device 110.

The terminal(s) 140 may be connected to and/or communicate with the imaging device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the imaging system 100. In some embodiments, one or more components of the imaging system 100 (e.g., the imaging device 110, the processing device 120, the storage device 130, the terminal(s) 140, etc.) may communicate information and/or data with one or more other components of the imaging system 100 via the network 150. For example, the processing device 120 and/or the terminal 140 may obtain PET data from the imaging device 110 via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the Imaging system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the imaging system 100 may include one or more additional components and/or one or more components of the imaging system 100 described above may be omitted. Additionally or alternatively, two or more components of the imaging system 100 may be integrated into a single component. A component of the imaging system 100 may be implemented on two or more sub-components.

Figure 2:
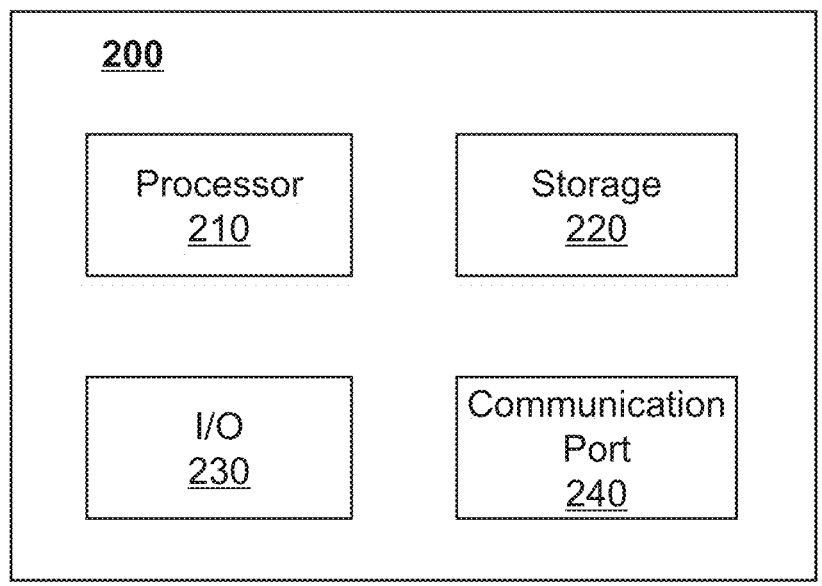
FIG. 2 is a schematic diagram illustrating exemplary hardware and/or software components of an exemplary computing device on which the processing device may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process imaging data obtained from the imaging device 110, the terminal(s) 140, the storage device 130, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the imaging device 110, the terminal(s) 140, the storage device 130, and/or any other component of the Imaging system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

Figure 3:
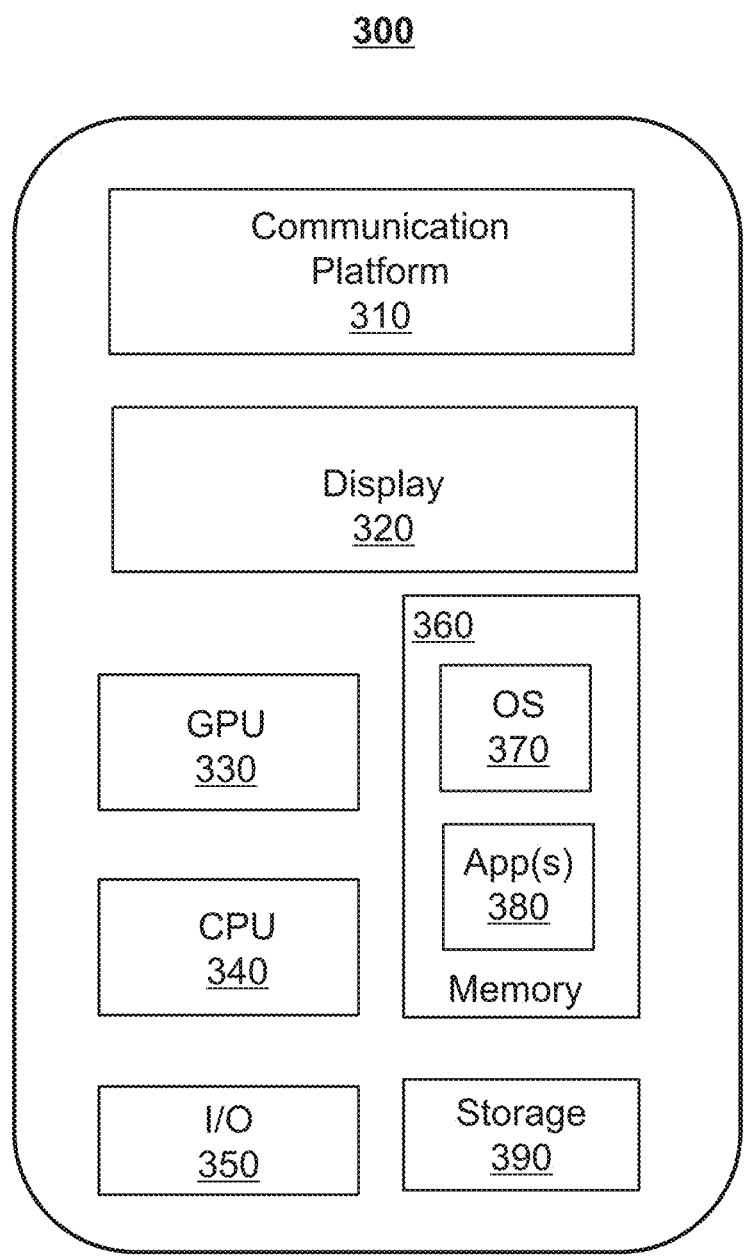
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 according to some embodiments of the present disclosure. In some embodiments, a terminal(s) 140 and/or a processing device 120 may be implemented on a mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the imaging system 100, and enable data and/or signal to be transmitted between the mobile device 300 and other components of the imaging system 100. For example, the communication platform 310 may establish a wireless connection between the mobile device 300 and the imaging device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the imaging system 100. For example, the communication platform 310 may transmit data and/or signals inputted by a user to other components of the imaging system 100. The inputted data and/or signals may include a user instruction. As another example, the communication platform 310 may receive data and/or signals transmitted from the processing device 120. The received data and/or signals may include imaging data acquired by a detector of the imaging device 110.

In some embodiments, a mobile operating system (OS) 370 (e.g., iOS™ Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information respect to motion signal recalibration or other information from the processing device 120. User interactions with the information stream may be achieved via the I/O 350 and provided to the processing device 120 and/or other components of the Imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
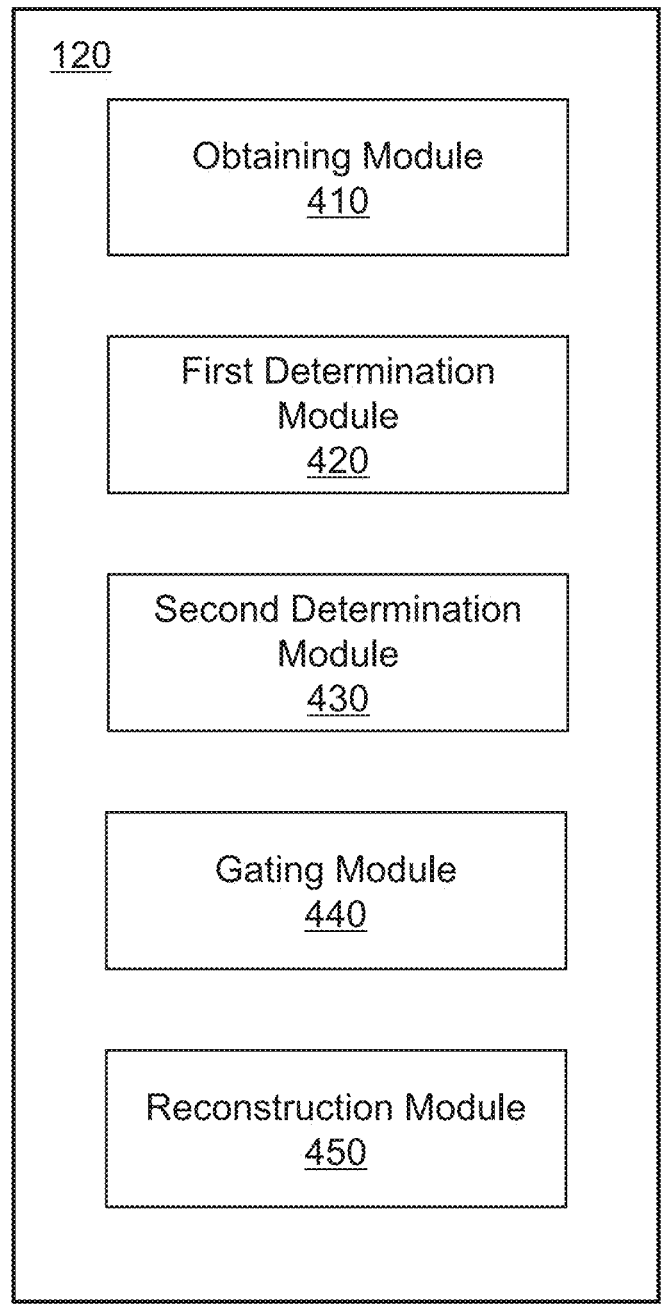
FIG. 4 is a schematic diagram illustrating an exemplary processing device according to some embodiments of the present disclosure.

FIG. 4 is a block diagram illustrating an exemplary processing device according to some embodiments of the present disclosure. In some embodiments, the processing device 120 may include an obtaining module 410, a first determination module 420, a second determination module 430, a gating module 440, and a reconstruction module 450.

The obtaining module 410 may be configured to obtain data and/or information associated with the imaging system 100. The data and/or information associated with the imaging system 100 may include PET data of a subject, a motion signal of the subject, an attenuation map, a motion amplitude threshold, or the like, or any combination thereof. For example, the obtaining module 410 may obtain PET data of a subject. As another example, the obtaining module 410 may obtain a motion signal of a subject. In some embodiments, the obtaining module 410 may obtain the data and/or the information associated with the imaging system 100 from one or more components (e.g., the terminal device 140, the storage device 130, the imaging device 110) of the imaging system 100 via the network 150.

The first determination module 420 may be configured to determine motion amplitude data. The motion amplitude data may indicate motion information (e.g., a motion range) for each voxel of a plurality of voxels in a reconstructed image domain. In some embodiments, the first determination module 420 may determine motion amplitude data based on an attenuation map. In some embodiments, the first determination module 420 may determine a plurality of intermediate images based on PET data. The first determination module 420 may determine a vector field for a plurality of voxels based on the plurality of intermediate images. The first determination module 420 may determine motion amplitude data based on the vector field. More descriptions for determining the motion amplitude data may be found elsewhere in the present disclosure (e.g., FIG. 5 and descriptions thereof).

The second determination module 430 may be configured to determine gating data based at least in part on motion amplitude data. The gating data may include useful percentage counts each of which corresponds to at least one voxel of a plurality of voxels in a reconstructed image domain. In some embodiments, the second determination module 430 may determine gating data based on motion amplitude data and a motion amplitude threshold. For example, the second determination module 430 may determine first processed motion amplitude data by performing a maximum intensity projection operation on motion amplitude data. The second determination module 430 may determine gating data based on the first processed motion amplitude data and a motion amplitude threshold. As another example, the second determination module 430 may determine second processed motion amplitude data by performing a projection operation on motion amplitude data. The second determination module 430 may determine gating data based on the second processed motion amplitude data and a motion amplitude threshold. More descriptions for determining the gating data may be found elsewhere in the present disclosure (e.g., FIG. 5 and descriptions thereof).

The gating module 440 may be configured to gate PET data based on gating data and a motion signal. In some embodiments, the gating module 440 may gate PET data (e.g., projection data) based on a plurality of useful percentage counts and a motion signal. More descriptions for gating the PET data may be found elsewhere in the present disclosure (e.g., FIG. 5 and descriptions thereof).

The reconstruction module 450 reconstruct a PET image of a subject based on gated PET data. In some embodiments, the reconstruction module 450 may use a reconstruction algorithm to reconstruct a gated PET image. More descriptions for reconstructing a PET image may be found elsewhere in the present disclosure (e.g., FIG. 5 and descriptions thereof).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the first determination module 420 and the second determination module 430 may be combined into a single module, which may both determine motion amplitude data and the gating data. In some embodiments, one or more modules may be added or omitted in the processing device 120. For example, the processing device 120 may further include a storage module (not shown in FIG. 4) configured to store data and/or information (e.g., the PET data, the motion signal, the motion amplitude data, the gating data, the PET image) associated with the imaging system 100.

Figure 5:
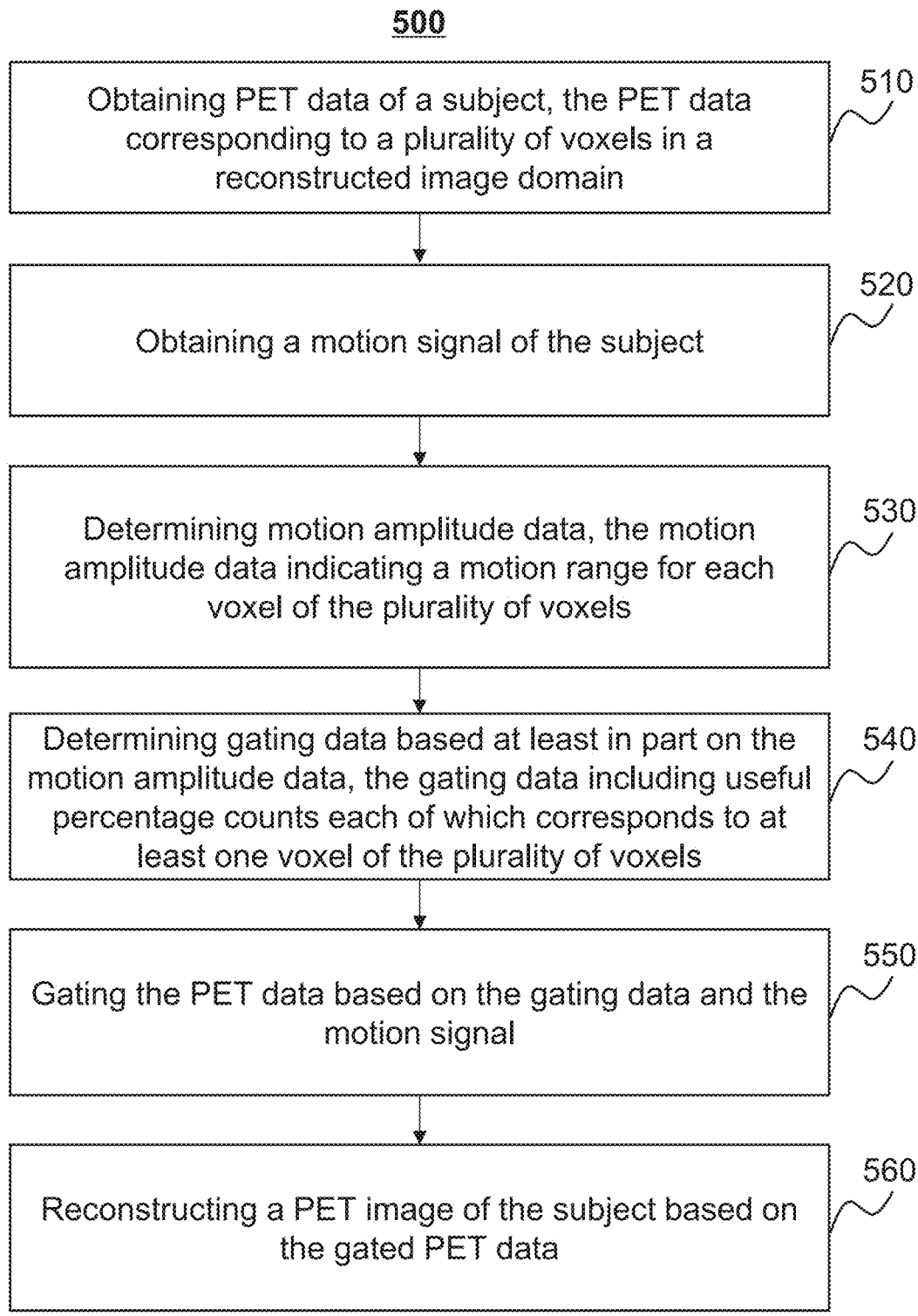
FIG. 5 is a flowchart illustrating an exemplary process for reconstructing a PET image according to some embodiments of the present disclosure.

FIG. 5 is a flowchart illustrating an exemplary process for reconstructing a PET image according to some embodiments of the present disclosure. In some embodiments, the process 500 may be implemented in the imaging system 100 illustrated in FIG. 1. For example, the process 500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain PET data of a subject. The PET data may correspond to a plurality of voxels in a reconstructed image domain. The plurality of voxels may correspond to a plurality of spatial points of the subject.

The PET data may be in a rawdata domain. In some embodiments, the PET data may be list-mode data or sinogram data. In some embodiments, the PET data may be four-dimensional (4D) projection data and stored in a list-mode format. As used herein, 4D data refers to a data form containing time domain data and 3D spatial data. For example, the PET data may be arranged based on a time axis.

In some embodiments, during a PET scan or analysis, a PET tracer (also referred to as "PET tracer molecules" or "tracer") are first introduced into the subject before an imaging process begins. During the PET scan, the PET tracer molecules may emit positrons, namely the antiparticles of electrons. A positron has the same mass and the opposite electrical charge of an electron, and it undergoes an annihilation (also referred to as an "annihilation event" or a "coincidence event") with an electron (that may naturally exist in abundance within the subject) as the two particles collide. An electron-positron annihilation may result in two particles (e.g., two 511 keV gamma photons), which, upon their own generation, begin to travel in opposite directions with respect to one another. The line connecting the two particles may be referred to as a "line of response (LOR)." The processing device 120 may obtain from detector units information regarding the trajectory and/or information (e.g., time) of the particles (also referred to as the "PET data"). For example, the PET data may include a list of annihilation events (also referred to as "PET counts"), transverse and longitudinal positions of the LORs, or the like, or any combination thereof.

In some embodiments, the PET data may include time of flight (TOF) information. The TOF information of a coincidence event may include a time difference (e.g., a TOF difference) between two detection times of two particles generated in the coincidence event, an estimated annihilation location on an LOR where the two particles are generated in the coincidence event (or an estimated annihilation location on an LOR at which a positron-electron annihilation corresponding to the coincidence event takes place), or the like, or any combination thereof. The estimated annihilation location may be determined based on the TOF difference and the speed of the particles that travel within the subject (e.g., speed of light). The estimated annihilation location of a coincidence event may indicate a probability distribution of annihilation location on the LOR at which two particles are generated in the coincidence event.

In some embodiments, the processing device 120 may obtain the PET data from one or more components (e.g., the imaging device 110, the terminal 140, and/or the storage device 130) of the imaging system 100 or an external storage device via the network 150. For example, the imaging device 110 may transmit acquired PET data (e.g., projection data) to the storage device 130, or any other storage device for storage. The processing device 120 may obtain the PET data from the storage device 130, or any other storage device. As another example, the processing device 120 may obtain the PET data from the imaging device 110 directly. In some embodiments, the processing device 120 may obtain the PET data in real time—essentially at the same as when the data is being collected. In some embodiments, the processing device 120 may obtain the PET data (e.g., from a storage device) after data has been collected for a period of time.

In 520, the processing device 120 (e.g., the obtaining module 410) may obtain a motion signal of the subject.

In some embodiments, the subject may undergo a motion (e.g., a respiratory motion, a cardiac motion) during the PET scan. The motion signal may reflect a motion state of a subject. For example, a respiratory motion signal may reflect the motion of tissue or an organ that is caused or influenced by the respiratory motion of a subject. A cardiac motion signal may reflect the motion of tissue or an organ that is caused or influenced by the motion of the heart of a subject.

In some embodiments, the processing device 120 may obtain the motion signal based on the PET data. For example, the processing device 120 may extract the respiratory motion signal from the PET data based on a data-driven technique. Exemplary data-driven techniques may include an approach based on a center of mass, an approach based on counts levels, an approach of a principal component analysis (PCA), or the like, or any combination thereof. For example, a coincidence counts versus time curve may be determined, thus providing an estimated respiratory motion signal. As another example, a center of mass of, for example, a distribution of PET tracers inside a VOI may be derived from the PET data. Then, a displacement of the center of mass as a function of time may provide a respiratory motion signal. As a further example, a principal component analysis (PCA) may be applied to the listmode PET data. Then, a respiratory motion signal may be obtained as the principal component weight factor whose frequency spectrum has the highest peak in the frequency band of a respiratory motion.

In some embodiments, the imaging system 100 may include a device for detecting a motion of the subject, a marker on a surface of the subject for indicating a motion of the subject, or the like, or any combination thereof. For example, the imaging system 100 may include a motion detection device, such as a gating camera (e.g., an infrared camera), a belt secured around the chest of the subject, or another pressure measurement technique or device to measure the change of pressure during the breathing cycles of the subject. The processing device 120 may obtain the motion signal of the subject from the motion detection device. In some embodiments, the processing device 120 may obtain the motion signal during or after the scanning, and/or before image reconstruction.

In some embodiments, the motion signal (e.g., the respiration signal) may correspond to a plurality of motion phases (e.g., respiratory phases) of the subject. In some embodiments, the respiratory phases of the subject (e.g., a patient) may include an intermediate inspiration phase, an end-inspiration phase, an intermediate expiration phase, an end-expiration phase, or the like, or any combination thereof. The intermediate inspiration phase and the end-inspiration phase may also be referred to as an inspiration phase. The intermediate expiration phase and the end-expiration phase may also be referred to as an expiration phase. For example, in the inspiration phase, the patient may expand his/her chest to cause a negative pressure in the chest. The negative pressure may cause the air to flow into the lungs of the patient. As another example, in the expiration phase, the patient may shrink the chest to cause a positive pressure in the chest. The positive pressure may push the air out of the lungs.

In 530, the processing device 120 (e.g., the first determination module 420) may determine motion amplitude data.

The motion amplitude data may indicate motion information (e.g., a motion range) for each voxel of the plurality of voxels. The motion range of a specific voxel may correspond to a motion range of a corresponding spatial point of the subject. In some embodiments, the motion amplitude data may be represented by A(x, y, z), wherein A refers to a motion range of a voxel with coordinates of (x, y, z).

In some embodiments, different regions of the subject may be affected differently (e.g., to different extents) by the motion of the subject. For example, the subject may include a first region and a second region. The first region may be affected more by the respiratory motion of the subject than the second region. For example, the first region may be a thoracic and abdominal region of the subject. The second region may be a region outside the thoracic and abdominal region of the subject. When the subject breaths during a scan, internal organs within the thoracic and abdominal region may move (the movement may be referred to as a respiratory motion). The region outside the thoracic and abdominal region may undergo no or little respiratory motion. Thus, the first region may be regarded as being affected more by the respiratory motion than the second region. Accordingly, the motion range of the voxel(s) corresponding to the first region may be greater than the motion range of the voxel(s) corresponding to the second region.

In some embodiments, the processing device 120 may determine a relationship between a region (e.g., an organ, tissue) of the subject and motion information (e.g., the motion range) of the region. The processing device 120 may determine the motion amplitude data based on the relationship between the region of the subject and motion information of the region. For example, the processing device 120 may determine the relationship between the region and the motion information of the region based on statistical data and/or clinical data of a plurality of sample subjects. The plurality of sample subjects may be of other persons having a similar characteristic compared to the subject (e.g., people of a similar height, weight, age, having a similar health condition, etc.). The statistical data and/or the clinical data may include a plurality of regions and a plurality of values of the motion range corresponding to the plurality of regions. The processing device 120 may determine the relationship based on a model (e.g., a trained machine learning model) or by performing at least one of a mapping operation, a model training operation, or the like, or any combination thereof, on the plurality of regions and the plurality of values of the motion range corresponding to the plurality of regions. For example, the relationship may be presented in the form of a table recording the plurality of regions and their corresponding values of the motion range. As another example, the relationship may be presented in the form of a motion model. A plurality of training samples may be obtained with respect to a plurality of regions and their corresponding values of the motion ranges of sample subjects. The motion model may be obtained by training a preliminary model using the training samples according to a machine learning algorithm (e.g., an artificial neural network algorithm, a deep learning algorithm, a decision tree algorithm).

The processing device 120 may then determine the motion range of each of a plurality of spatial points of the subject based on the relationship between regions of the subject and the motion information of the region. For example, the processing device 120 may determine the motion range of a region to which the spatial point belongs as the motion range of the spatial point. The processing device 120 may further designate the motion range of the spatial point of the subject as the motion range of a voxel in the reconstructed image domain corresponding to the spatial point.

In some embodiments, the processing device 120 may obtain an attenuation map of the subject. The processing device 120 may determine the motion amplitude data based on the attenuation map. In some embodiments, the attenuation map including a plurality of attenuation coefficients may be determined based on a CT image. Additionally or alternatively, the attenuation map may be determined based on an MRI image. The MRI image may provide anatomical data of the subject. Attenuation coefficients of different portions may be assigned to corresponding portions of the MRI image to generate the attenuation map. Merely by way of example, the attenuation coefficient may be a tissue attenuation coefficient corresponding to the γ ray in an energy level of 511 KeV. In some embodiments, different regions of the subject may correspond to different attenuation coefficients. The processing device 120 may identify the region of the subject based on the attenuation coefficients in the attenuation map. In some embodiments, one or more specific regions (e.g., a lung region, a liver region, an abdomen region) of the subject may be considered affected by the motion of the subject, and other regions may be considered unaffected by the motion of the subject. The processing device 120 may determine the motion range for the voxel based on the relationship between the region of the subject and the motion information of the region, and the region to which the voxel belongs.

In some embodiments, the processing device 120 may determine a plurality of intermediate images based on the PET data. The plurality of intermediate images may correspond to the same spatial points in the scanning of the subject. The processing device 120 may determine the motion amplitude data based on the plurality of intermediate images.

In some embodiments, the plurality of intermediate images may be reconstructed by gating the PET data. For example, the processing device 120 may gate the PET data into a plurality of groups or bins according to a uniform gate number. Different groups may correspond to different time periods or phases of the motion (e.g., the respiratory motion, the cardiac motion). For example, different groups may correspond to different respiratory phases of the subject. The processing device 120 may reconstruct the plurality of intermediate images using the plurality of groups of gated PET data. For illustration purposes, a first group of gated PET data may correspond to an end inspiration phase, and a second group of gated PET data may correspond to an end-expiration phase. The processing device 120 may reconstruct a first intermediate image using the first group of gated PET data and a second intermediate image using the second group of gated PET data.

In some embodiments, the plurality of intermediate images may be determined by performing a back-projection operation on the gated PET data. For example, the PET data may be 4D projection data and stored in the listmode format. The plurality of intermediate images may be reconstructed by performing the back-projection operation on the PET data acquired at different motion phases. In some embodiments, a PET scan may be performed during at least two cycles of the respiratory motion. PET data acquired at different time periods that belong to a same motion phase of the respiratory motion may be merged into a same group or bin used to construct an intermediate image.

The processing device 120 may determine a vector field for the plurality of voxels based on the plurality of intermediate images. In some embodiments, the processing device 120 may determine the vector field by registering the plurality of intermediate images. For example, the processing device 120 may register the first intermediate image and the second intermediate image based on a registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, or the like, or any combination thereof.

The motion vector field may include a plurality of motion vectors. A motion vector may be used to describe the motion information (e.g., a motion range or amplitude, a motion direction) of a spatial point of the subject between different motion phases as represented in different intermediate images (e.g., in the first intermediate image and the second intermediate image). The processing device 120 may determine the motion amplitude data based on the vector field. For example, the processing device 120 may determine a first location of a spatial point in the first intermediate image to be $(X_1, Y_1, Z_1)$, and a second location of the spatial point in the second intermediate image to be $(X_2, Y_2, Z_2)$. The processing device 120 may further determine a motion vector to be (Ux, Uy, Uz) based on the first location and the second location of the spatial point, where Ux may be equal to $(X_1-X_2)$, Uy may be equal to $(Y_1-Y_2)$, and Uz may be equal to $(Z_1-Z_2)$. The motion vector (Ux, Uy, Uz) corresponding to the spatial point may be regarded as the motion amplitude data for a voxel corresponding to the spatial point.

In 540, the processing device 120 (e.g., the second determination module 430) may determine gating data based at least in part on the motion amplitude data. The gating data may include useful percentage counts each of which corresponds to at least one voxel of the plurality of voxels.

As used herein, a useful percentage count corresponding to a specific voxel refers to a ratio of saved PET counts to all the acquired PET counts corresponding to the specific voxel. The saved PET counts may be used to reconstruct the specific voxel. In some embodiments, the useful percentage count corresponding to the voxel may relate to the motion amplitude data corresponding to the voxel. A relatively high motion range or amplitude for the voxel may correspond to a relatively low useful percentage count corresponding to the voxel.

For illustration purposes, a first motion range for a first voxel may correspond to a first useful percentage count, and a second motion range for a second voxel may correspond to a second useful percentage count. The first useful percentage count may be different from the second useful percentage count. For example, the first motion range is greater than the second motion range, and the first useful percentage count may be lower than the second useful percentage count.

Accordingly, for a voxel (corresponding to a spatial point) with a higher motion range during the scan of the subject, lower counts corresponding to the voxel may be saved for image reconstruction, which may reduce motion artifacts and blurring in a reconstructed PET image caused by the motions of a spatial point of the subject corresponding to the voxel. For a voxel (corresponding to a spatial point) with a lower motion range during the scan of the subject, more counts corresponding to the voxel may be saved for image reconstruction, which may reduce noise in the reconstructed PET image caused by unnecessary over-gating.

In some embodiments, the processing device 120 may obtain a motion amplitude threshold. The processing device 120 may then determine the gating data based on the motion amplitude data and the motion amplitude threshold. The motion amplitude threshold may relate to a spatial resolution of a PET system that obtains the PET data. Additionally or alternatively, the motion amplitude threshold may relate to a reconstruction parameter of a PET image (e.g., a desired spatial resolution of a reconstructed PET image). For example, a relatively low desired spatial resolution of a reconstructed PET image may correspond to a relatively high motion amplitude threshold. The motion amplitude threshold may be manually set based on an instruction provide by a user of the imaging system 100 or determined by one or more components (e.g., the processing device 120) of the imaging system 100 according to different situations.

In some embodiments, the PET data may include TOF information. The PET data may correspond to a plurality of LORs. Each LOR of the plurality of LORs may include a plurality of bins. Each bin of the plurality of bins may correspond to at least one voxel of the plurality of voxels. A length of each bin may relate to the TOF information (e.g., a TOF resolution). For example, the length of the each bin may be equal to a product of the TOF resolution and the speed of light. For each LOR of the plurality of LORs, the processing device 120 may determine the useful percentage count for each bin of the plurality of bins based on the motion amplitude data and the motion amplitude threshold. In some embodiments, the PET data may lack TOF information. For each LOR of the plurality of LORs, the processing device 120 may determine the useful percentage count for the LOR based on the motion amplitude data and the motion amplitude threshold. More descriptions of the gating data may be found elsewhere in the present disclosure (e.g., FIGS. 6B, 6C, and descriptions thereof).

In some embodiments, for each voxel of the plurality of voxels, the processing device 120 may determine a useful percentage count for the voxel based on a motion range for the voxel and the motion amplitude threshold. Merely by way of example, the processing device 120 may determine a useful percentage count for a voxel (x, y, z) according to Equation (1):

$$C(x, y, z) = \min\left(\frac{A_0}{A(x, y, z)}, 1\right) * 100\%, \quad (1)$$

where C(x, y, z) refers to the useful percentage count for the voxel (x, y, z); $A_0$ refers to the motion amplitude threshold; and A(x, y, z) refers to a motion range for the voxel (x, y, z). In a conventional gating technology (i.e., an equal amplitude gating technology), a gate number N may be equal to max (A (x, y, z))/$A_0$, and the useful percentage counts may be $A_0$/max (A (x, y, z))*100%. For a locally adaptive gating technology as described in the present disclosure, the useful percentage counts for the voxels determined based on the motion ranges for the voxels may be spatially variant.

In some embodiments, the processing device 120 may determine first processed motion amplitude data by performing a maximum intensity projection operation on the motion amplitude data. The processing device 120 may determine the gating data based on the first processed motion amplitude data and the motion amplitude threshold. Merely by way of example, the processing device 120 may determine useful percentage counts for PET sinogram data R(s, θ, ζ) according to Equation (2):

$$R(s, \theta, \zeta) = \min\left(1, \frac{A_0}{M(A(x, y, z))}\right) * 100\%, \quad (2)$$

where (s, θ, ζ) refers to 3D sinogram coordinates; and M(•) refers to a maximum intensity projection operation.

In some embodiments, the processing device 120 may determine second processed motion amplitude data in the rawdata domain by performing a projection operation on the motion amplitude data. The processing device 120 may determine the gating data based on the second processed motion amplitude data and the motion amplitude threshold. In some embodiments, for the PET data with TOF information, due to the generally low spatial resolution of the motion information, the motion amplitude may be assumed to be constant within each TOF kernel. Merely by way of example, the processing device 120 may determine the useful percentage counts for PET sinogram data R(s, θ, ζ) with TOF information according to Equation (3):

$$R(s, \theta, \zeta, \tau) = \min\left(1, \frac{A_0 L}{P(A(x, y, z))}\right) * 100\%, \quad (3)$$

where P(•) refers to a projection operation; L refers to a summation of the TOF kernel; (s, θ, ζ) refers to sinogram coordinates; and τ refers to a TOF coordinate. In some embodiments, the summation of the TOF kernerl may be a normalization coefficient. As used herein, a TOF kernel may represent a probability distribution of an annihilation point along a TOF direction. In some embodiments, the summation of the TOF kernerl may be 1. The TOF coordinate may be associated with an estimated annihilation location on a LOR where the two particles are generated in the coincidence event (e.g., a location of a peak of a probability distribution of annihilation location on the LOR at which two particles are generated in the coincidence event). The replacement of M(•) involved in Equation (2) with P(•) involved in Equation (3) may make simplify the determination of useful percentage counts for PET sinogram data given an existing reconstruction algorithm.

In 550, the processing device 120 (e.g., the gating module 440) may gate the PET data based on the gating data and the motion signal.

In some embodiments, the processing device 120 may gate the PET data (e.g., projection data) based on the plurality of useful percentage counts and the motion signal. For example, for a specific voxel, the processing device 120 may gate the projection data acquired from a spatial point corresponding to the specific voxel along the time axis according to the useful percentage count corresponding to the specific voxel.

Merely by way of example, in a conventional gating where a certain percentage N of counts (e.g., 20% counts in which N=20% or 0.2) and a reference phase $g_0$ are used, the gating operation may be represented as:

$$P_{g_0}(s, \theta, \zeta) = \int_{g_0-N/2}^{g_0+N/2} P(s, \theta, \zeta, g)dg, \quad (4)$$

where $g_0$ refers to a reference motion phase; (s, θ, ζ) refers to sinogram coordinates; P(s, θ, ζ, g) refers to gated PET sinogram data; and g refers to a gating coordinate representing a motion phase.

In some embodiments, in the locally adaptive gating technology as described in the present disclosure, for each PET count of a plurality of PET counts acquired at a given time, the processing device 120 may determine whether the PET count is excluded or included based on the gating data and the motion signal. For example, if a PET count is obtained in a time period in which the subject is largely affected by the motion (e.g., the respiratory motion, the cardiac motion), the processing device 120 may determine that the PET count is excluded. If a PET count is obtained in a time period in which the subject is not or little affected by the motion, the processing device 120 may determine that the PET count is included. In response to determining that the PET count is excluded, the PET count may be deleted. In response to determining that the PET count is included, the PET count may be saved and used for reconstructing a PET image of the subject. For illustration purposes, if a plurality of PET counts are acquired in a time period of 0~10 s, the entire motion amplitude range of the subject in the time period of 0~10 s is 10 mm, and the motion amplitude range of the subject in the time period of 0~2 s is 2 mm, the PET counts acquired in the time period of 0~2 s may be saved.

Merely by way of example, the gating operation may be represented as:

$$P_{L-g_0}(s, \theta, \zeta) = \int_{g_0-R(s,\theta,\zeta)/2}^{g_0+R(s,\theta,\zeta)/2} P(s, \theta, \zeta, g)dg, \quad (5)$$

where $g_0$ refers to a reference motion phase; (s, θ, ζ) refers to sinogram coordinates; P(s, θ, ζ, g) refers to gated PET sinogram data; g refers to a gating coordinate, 0≤g≤1; and R(s, θ, ζ) refers to gating data (e.g., useful percentage of counts for the PET sinogram data). Taking a respiratory gating as an example, if g=0.5 corresponds to an end-inspiration phase, and g=1 or g=0 corresponds to an end-expiration phase, P(s, θ, ζ, g) may be a periodic function for g. That is, P(s, θ, ζ, 1+g)=P(s, θ, ζ, g).

In 560, the processing device 120 (e.g., the reconstruction module 450) may reconstruct a PET image of the subject based on the gated PET data.

In some embodiments, the processing device 120 may use a reconstruction algorithm to reconstruct a gated PET image. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

In some embodiments, in a conventional gating technology (i.e., an equal amplitude gating technology), the PET image of the subject may be reconstructed according to Equation (6):

$$\lambda_i^{n+1} = \frac{\lambda_i^n}{\Sigma_j H_{i,j}} \Sigma_j H_{i,j} \frac{p_j}{\Sigma_i H_{i,j} \lambda_i^n + r_j}, \quad (6)$$

where $\Delta_i^n$ refers to a reconstructed image of the nth iteration; i refers to image coordinates (x, y, z); H refers to a projection matrix; r refers to a sum of scattering and random effects; j refers to sinogram coordinates (s, θ, ζ); and $p_j$ refers to gated PET sinogram data.

In some embodiments, in the local gating technology as described in the present disclosure, the processing device 120 may reconstruct the PET image of the subject based on the gated PET data and the gating data. Merely by way of example, the processing device 120 may reconstruct the PET image according to Equation (7):

$$\lambda_i^{n+1} = \frac{\lambda_i^n}{\Sigma_j R_j H_{i,j}} \Sigma_j H_{i,j} \frac{p_j}{\Sigma_i H_{i,j} \lambda_i^n + r_j}, \quad (7)$$

where $\lambda_i^n$ refers to a reconstructed image of the nth iteration; i refers to image coordinates (x, y, z); H refers to a projection matrix; r refers to a sum of scattering and random effects; j refers to sinogram coordinates (s, θ, ζ); $p_j$ refers to gated PET sinogram data; and $R_j$ refers to gating data (e.g., useful percentage of counts for the PET sinogram data).

As another example, the processing device 120 may reconstruct the PET image according to Equation (8):

$$\lambda_i^{n+1} = \frac{\lambda_i^n}{\Sigma_j H_{i,j}} \Sigma_j H_{i,j} \frac{p_j/R_j}{\Sigma_i H_{i,j} \lambda_i^n + r_j}, \quad (8)$$

where $\lambda_i^n$ refers to a reconstructed image of the nth iteration; i refers to image coordinates (x, y, z); H refers to a projection matrix; r refers to a sum of scattering and random effects; j refers to sinogram coordinates (s, θ, ζ); $p_j$ refers to gated PET sinogram data; and $R_j$ refers to gating data (e.g., useful percentage of counts for the PET sinogram data).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operation 510 and operation 520 may be performed simultaneously. As another example, operation 520 may be performed before operation 510. As still another example, operation 520 may be performed after operation 540 and before operation 550. In some embodiments, the processing device 120 may determine a sensitivity map based on the gating data. For example, the processing device 120 may determine the sensitivity map by performing a back-projection operation on the gating data R(s, θ, ζ).

In some embodiments, the PET data may be listmode data. In the listmode data, an event may contain spatial information and temporal information, which may be represented as (s, θ, ζ, τ, t), wherein (s, θ, ζ, τ) refer to spatial coordinates, and t refers to a time coordinate. A motion curve indicating a motion amplitude at a time point t may be represented as S(t), wherein 0≤(t)≤1. Motion amplitude data M(A(x, y, z)) may be determined by performing a projection operation M on the motion amplitude data A(x, y, z), and also be represented as $A_s$(s, θ, ζ, τ). Each event may correspond to a motion amplitude $A_s$(s, θ, ζ, τ)*S(t). For each event of a plurality events, the processing device 120 may determine whether the motion amplitude $A_s$(s, θ, ζ, τ)*S(t) corresponding to the event is less than the motion amplitude threshold $A_0$. In response to determining that the motion amplitude $A_s$(s, θ, ζ, τ)*S(t) corresponding to the event is less than or equal to the motion amplitude threshold $A_0$, the event may be saved. In response to determining that the motion amplitude $A_s$(s, θ, ζ, τ)*S(t) corresponding to the event is greater than the motion amplitude threshold $A_0$, the event may be deleted.

Figure 6A:
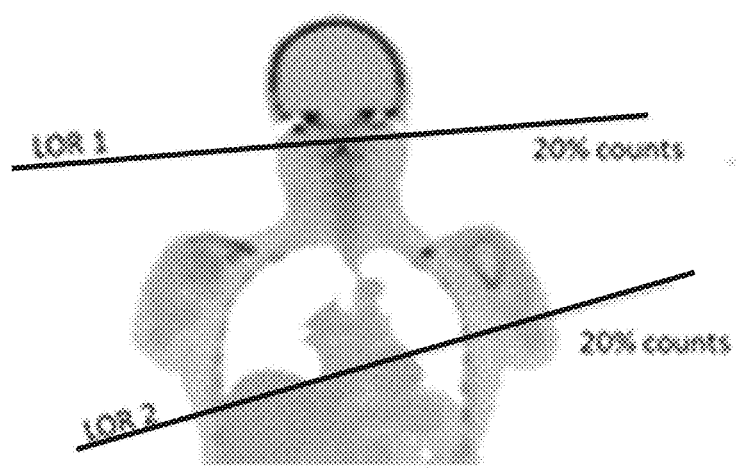
FIG. 6A illustrates exemplary gating data determined in a conventional gating technique.
Figure 6B:
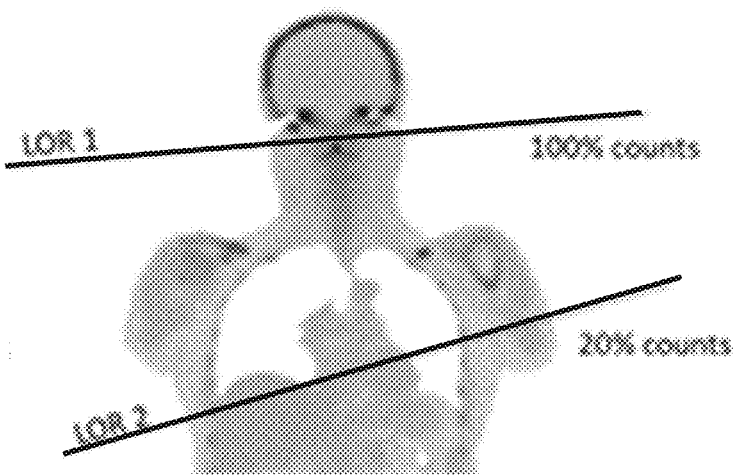
FIG. 6B illustrates exemplary gating data determined in a non-TOF based locally adaptive gating technique according to some embodiments of the present disclosure.
Figure 6C:
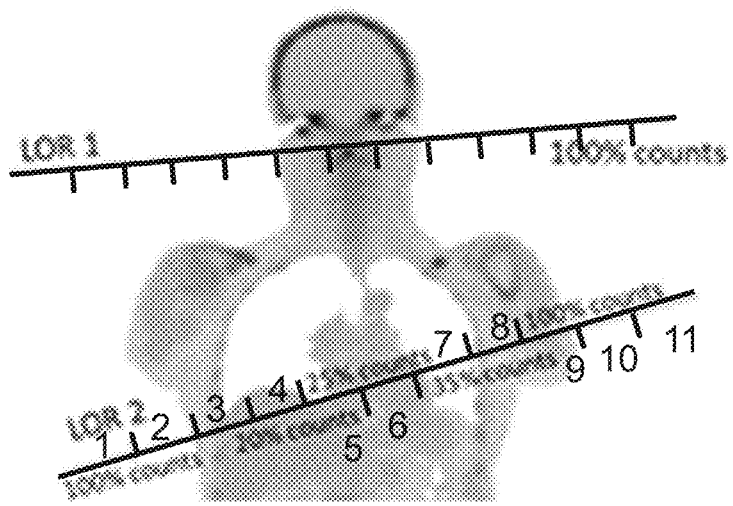
FIG. 6C illustrates exemplary gating data determined in a TOF based locally adaptive gating technique according to some embodiments of the present disclosure.

FIG. 6A illustrates exemplary gating data determined in a conventional gating technique. FIG. 6B illustrates exemplary gating data determined in a non-TOF based locally adaptive gating technique according to some embodiments of the present disclosure. FIG. 6C illustrates exemplary gating data determined in a TOF based locally adaptive gating technique according to some embodiments of the present disclosure.

As illustrated in FIG. 6A, in a conventional gating technique, a useful percentage count for each LOR of a plurality of LORs may be the same. For example, a first useful percentage count for a first LOR and a second useful percentage count for a second LOR may be both 20%. The first LOR may correspond to a first non-motion area (e.g., a head region) of a subject. The second LOR may correspond to a plurality of motion areas (e.g., a liver region, a heart region, a lung region) and a second non-motion area (e.g., an arm region) of the subject. The plurality of motion areas of the subject may move by various degrees during a PET scan of the subject.

As illustrated in FIG. 6B, in a non-TOF based locally adaptive gating technique according to some embodiments as described in the present disclosure, for PET data without TOF information, a useful percentage count for the each LOR of the plurality of LORs may be different. In some embodiments, the useful percentage counts for at least two of the plurality of LORs may be determined based on motion amplitude data and a motion amplitude threshold according to Equation (2) as described elsewhere in the present disclosure. For example, the first useful percentage count for the first LOR may be different from the second useful percentage count for the second LOR. The first useful percentage count for the first LOR corresponding to the head region may be 100%, and the second useful percentage count for the second LOR corresponding to the liver region, the heart region, the lung region, and the arm region may be 20%.

As illustrated in FIG. 6C, in a TOF based locally adaptive gating technique as described in the present disclosure, for PET data with TOF information, useful percentage counts for at least two of the plurality of LORs may be different. In some embodiments, each LOR of the plurality of LORs may include a plurality of bins. Each bin of the plurality of bins may correspond to at least one voxel of a plurality of voxels in a reconstructed image domain. The useful percentage counts for at least two bins corresponding to a same LOR of the plurality of LORs may be the same or different. In some embodiments, the useful percentage count for a bin of a LOR may be determined based on motion amplitude data and a motion amplitude threshold according to Equation (3) as described elsewhere in the present disclosure. For example, the first useful percentage count for each bin of the first LOR corresponding to the head region may be 100%. The second useful percentage count for each bin of the second LOR may be different. The second useful percentage counts for one or more bins correspond to the liver region (e.g., a bin 3, a bin 4), the heart region (e.g., a bin 5, a bin 6), the lung region (e.g., a bin 7, a bin 8), and the arm region (e.g., a bin 1, a bin 1, a bin 9, a bin 10, a bin 11) may be 20%, 25%, 35%, and 100%, respectively.

Figures 7A, 7B:
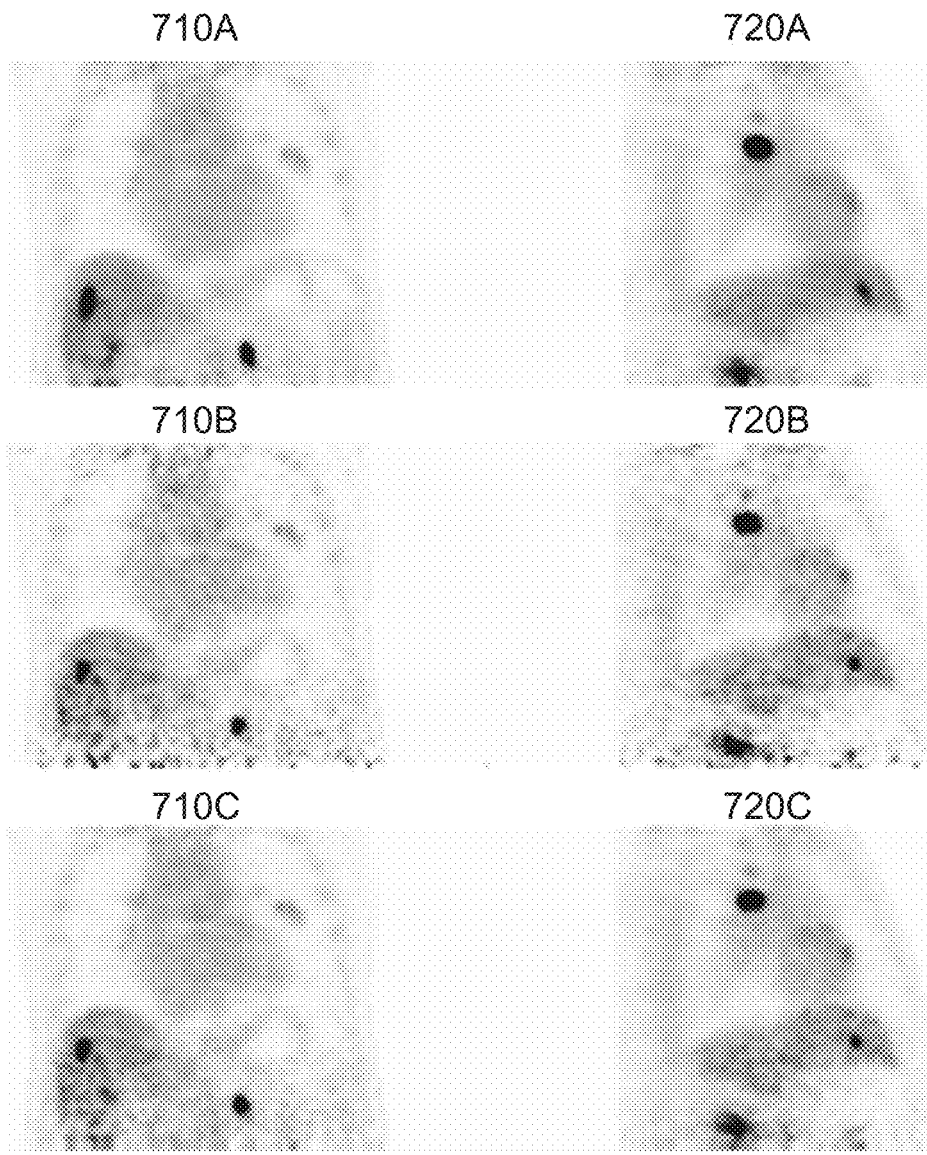
FIG. 7A illustrates exemplary PET images according to some embodiments of the present disclosure.
FIG. 7B illustrates exemplary PET images according to some embodiments of the present disclosure.

FIG. 7A illustrates exemplary PET images according to some embodiments of the present disclosure. As illustrated in FIG. 7A, 710A refers to a PET image reconstructed based on a non-gating technique, 710B refers to a PET image reconstructed based on PET data that was gated according to a uniform gate number (i.e., a same useful percentage count), and 710C refers to a PET image reconstructed according to process 500 described in the present disclosure. The PET image 710A, the PET image 710B, and the PET image 710C correspond to a same portion of a subject.

It may be seen that the PET image 710A has a relatively low noise level but a relatively poor image resolution. Compared with the PET image 710A, the PET image 710B has a relatively high image resolution and a relatively high noise level. The noise level of the PET image 710C is similar to PET image 710A. The image resolution of the PET image 710C is similar to the PET image 710B.

FIG. 7B illustrates exemplary PET images according to some embodiments of the present disclosure.

As illustrated in FIG. 7B, 720A refers to a PET image reconstructed based on a non-gating technique, 720B refers to a PET image reconstructed based on PET data that was gated according to a uniform gate number (i.e., a same useful percentage count), and 720C refers to a PET image reconstructed according to process 500 described in the present disclosure. The PET image 720A, the PET image 720B, and the PET image 720C correspond to a same portion of a subject.

It may be seen that the PET image 720A has a relatively low noise level but a relatively poor image resolution. Compared with the PET image 720A, the PET image 720B has a relatively high image resolution and a relatively high noise level. The noise level of the PET image 720C is similar to PET image 720A. The image resolution of the PET image 720C is similar to the PET image 720B.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for reconstructing a positron emission tomography (PET) image implemented on a computing device having at least one processor and at least one storage device, the method comprising:
    obtaining PET data of a subject, wherein
        the PET data corresponds to a plurality of lines of response (LORs), and
        each LOR of the plurality of LORs includes a plurality of bins, each bin of the plurality of bins corresponding to at least one voxel of a plurality of voxels in a reconstructed image domain;
    obtaining a motion signal of the subject;
    obtaining motion amplitude data, the motion amplitude data indicating a motion range for each voxel of the plurality of voxels;
    determining gating data based at least in part on the motion amplitude data, wherein
        the gating data includes a useful percentage count for the each bin of the plurality of bins,
        the useful percentage count for the each bin indicates a ratio of saved PET counts to all acquired PET counts corresponding to the each bin,
        the saved PET counts are obtained in a time period in which the motion range for the at least one voxel corresponding to the each bin is less than a threshold, and
        the saved PET counts are used for reconstructing the at least one voxel corresponding to the each bin;
    gating the PET data based on the gating data and the motion signal; and
    reconstructing a PET image of the subject based on the gated PET data.

2. The method of claim 1, wherein obtaining motion amplitude data comprises:
    obtaining an attenuation map of the subject; and
    determining the motion amplitude data based on the attenuation map.

3. The method of claim 1, wherein obtaining motion amplitude data comprises:
   determining a plurality of intermediate images based on the PET data;
   determining a vector field for the plurality of voxels based on the plurality of intermediate images; and
   determining the motion amplitude data based on the vector field.

4. The method of claim 3, wherein the plurality of intermediate images are determined by performing a back-projection operation on the PET data.

5. The method of claim 3, wherein the plurality of intermediate images are reconstructed by gating the PET data.

6. The method of claim 1, wherein determining gating data based on the motion amplitude data comprises:
   obtaining a motion amplitude threshold; and
   determining the gating data based on the motion amplitude data and the motion amplitude threshold.

7. The method of claim 6, wherein the motion amplitude threshold relates to a desired spatial resolution of the reconstructed PET image.

8. The method of claim 6, wherein determining the gating data based on the motion amplitude data and the motion amplitude threshold comprises:
   determining first processed motion amplitude data by performing a maximum intensity projection operation on the motion amplitude data; and
   determining the gating data based on the first processed motion amplitude data and the motion amplitude threshold.

9. The method of claim 6, wherein determining the gating data based on the motion amplitude data and the motion amplitude threshold comprises:
   determining second processed motion amplitude data by performing a projection operation on the motion amplitude data; and
   determining the gating data based on the second processed motion amplitude data and the motion amplitude threshold.

10. The method of claim 6, wherein determining the gating data based on the motion amplitude data and the motion amplitude threshold comprises:
    for each bin of the plurality of bins of the each LOR, determining a useful percentage count for the bin based on a motion range for the at least one voxel corresponding to the bin and the motion amplitude threshold.

11. The method of claim 6, wherein
    the PET data includes TOF information, and
    a length of each bin relates to the TOF information.

12. The method of claim 1, wherein
    a first motion range for at least one first voxel corresponding to a first bin corresponds to a first useful percentage count,
    a second motion range for at least one second voxel corresponding to a second bin corresponds to a second useful percentage count, and
    the first useful percentage count is different from the second useful percentage count.

13. The method of claim 12, wherein
    the first motion range is greater than the second motion range, and
    the first useful percentage count is lower than the second useful percentage count.

14. A system for reconstructing a positron emission tomography (PET) image, comprising:
    at least one storage device storing a set of instructions; and
    at least one processor in communication with the at least one storage device, when executing the stored set of instructions, the at least one processor causes the system to perform operations including:
       obtaining PET data of a subject, wherein
          the PET data corresponds to a plurality of lines of response (LORs), and
          each LOR of the plurality of LORs includes a plurality of bins, each bin of the plurality of bins corresponding to at least one voxel of a plurality of voxels in a reconstructed image domain;
       obtaining a motion signal of the subject;
       obtaining motion amplitude data, the motion amplitude data indicating a motion range for each voxel of the plurality of voxels;
       determining gating data based at least in part on the motion amplitude data, wherein
          the gating data includes a useful percentage count for the each bin of the plurality of bins,
          the useful percentage count for the each bin indicates a ratio of saved PET counts to all acquired PET counts corresponding to the each bin,
          the saved PET counts are obtained in a time period in which the motion range for the at least one voxel corresponding to the each bin is less than a threshold, and
          the saved PET counts are used for reconstructing the at least one voxel corresponding to the each bin;
       gating the PET data based on the gating data and the motion signal; and
       reconstructing a PET image of the subject based on the gated PET data.

15. The system of claim 14, wherein to obtain motion amplitude data, the at least one processor causes the system to perform operations including:
    obtaining an attenuation map of the subject; and
    determining the motion amplitude data based on the attenuation map.

16. The system of claim 14, wherein to obtain motion amplitude data, the at least one processor causes the system to perform operations including:
    determining a plurality of intermediate images based on the PET data;
    determining a vector field for the plurality of voxels based on the plurality of intermediate images; and
    determining the motion amplitude data based on the vector field.

17. The system of claim 16, wherein the plurality of intermediate images are determined by performing a back-projection operation on the PET data.

18. The system of claim 16, wherein the plurality of intermediate images are reconstructed by gating the PET data.

19. The system of claim 14, wherein to determine gating data based on the motion amplitude data, the at least one processor causes the system to perform operations including:
    obtaining a motion amplitude threshold; and
    determining the gating data based on the motion amplitude data and the motion amplitude threshold.

20. A non-transitory computer readable medium, comprising at least one set of instructions, wherein when executed by at least one processor of a computing device, the at least one set of instructions cause the at least one processor to effectuate a method comprising:

obtaining PET data of a subject, wherein
  the PET data corresponds to a plurality of lines of response (LORs), and
  each LOR of the plurality of LORs includes a plurality of bins, each bin of the plurality of bins corresponding to at least one voxel of a plurality of voxels in a reconstructed image domain;

obtaining a motion signal of the subject;

obtaining motion amplitude data, the motion amplitude data indicating a motion range for each voxel of the plurality of voxels;

determining gating data based at least in part on the motion amplitude data, wherein
  the gating data includes a useful percentage count for the each bin of the plurality of bins,
  the useful percentage count for the each bin indicates a ratio of saved PET counts to all acquired PET counts corresponding to the each bin,
  the saved PET counts are obtained in a time period in which the motion range for the at least one voxel corresponding to the each bin is less than a threshold, and
  the saved PET counts are used for reconstructing the at least one voxel corresponding to the each bin;

gating the PET data based on the gating data and the motion signal; and reconstructing a PET image of the subject based on the gated PET data.

\* \* \* \* \*